(12) United States Patent
Fink et al.

(10) Patent No.: US 8,444,559 B2
(45) Date of Patent: May 21, 2013

(54) SKIN IMPEDANCE MATCHING SYSTEM AND METHOD FOR SKIN/ELECTRODE INTERFACE

(75) Inventors: Rainer J. Fink, College Station, TX (US); Jack N. McCrary, Houston, TX (US)

(73) Assignee: Reproductive Research Technologies, LP, Houston, TX (US)

( * ) Notice: Subject to any disclaimer, the term of this patent is extended or adjusted under 35 U.S.C. 154(b) by 1217 days.

(21) Appl. No.: 12/114,490

(22) Filed: May 2, 2008

(65) Prior Publication Data
US 2008/0275316 A1    Nov. 6, 2008

Related U.S. Application Data

(60) Provisional application No. 60/916,202, filed on May 4, 2007.

(51) Int. Cl.
*A61B 5/053* (2006.01)

(52) U.S. Cl.
USPC .......................................................... 600/306

(58) Field of Classification Search
None
See application file for complete search history.

(56) References Cited

U.S. PATENT DOCUMENTS

| | | | |
|---|---|---|---|
| 3,703,168 A | 11/1972 | Frink |
| 4,256,118 A | 3/1981 | Nagel |
| 4,299,234 A | 11/1981 | Epstein et al. |
| 4,308,873 A | 1/1982 | Maynard |
| 4,577,640 A | 3/1986 | Hofmeister |
| 4,738,268 A | 4/1988 | Kipnis |
| 4,781,200 A | 11/1988 | Baker |
| 4,945,917 A | 8/1990 | Akselrod et al. |
| 4,967,761 A | 11/1990 | Nathanielsz |
| 5,042,499 A | 8/1991 | Frank et al. |
| 5,057,783 A | 10/1991 | Gubisch |
| 5,205,296 A | 4/1993 | Dukes et al. |
| 5,209,237 A | 5/1993 | Rosenthal |
| 5,217,022 A | 6/1993 | Nathanielsz |
| 5,301,680 A | 4/1994 | Rosenberg |
| 5,372,139 A | 12/1994 | Holls et al. |
| 5,397,344 A | 3/1995 | Garfield et al. |
| 5,400,799 A | 3/1995 | Yoches |
| 5,447,526 A | 9/1995 | Karsdon |

(Continued)

FOREIGN PATENT DOCUMENTS

WO    03090366 A3    10/2003

OTHER PUBLICATIONS

Demianczuk et al., Am. J. Obstet. Gynecol., vol. 149, No. 5, pp. 484-491 pp. 485-491 (Jul. 1, 1984).

(Continued)

*Primary Examiner* — Shanon A Foley
(74) *Attorney, Agent, or Firm* — Hulsey, P.C.; Loren T. Smith; William N. Hulsey, III

(57) ABSTRACT

The present invention relates to a system for measuring the input impedance of a skin/electrode interface and selectively modifying the input impedance of the monitoring circuit to match the measured input impedance. More particularly, a simplified method for correcting for input impedance mismatch between electronic monitoring circuitry and the skin/electrode interface. In accordance with one embodiment of the invention, an input impedance measuring circuit will interface with a microprocessor and a reconfigurable switch network to select the input impedance of the electronic monitoring circuitry, thus eliminating the impedance sensitivity of EMG or EKG instruments.

14 Claims, 2 Drawing Sheets

U.S. PATENT DOCUMENTS

| | | | |
|---|---|---|---|
| 5,483,970 A | 1/1996 | Rosenberg | |
| 5,522,877 A | 6/1996 | Garfield et al. | |
| 5,546,953 A | 8/1996 | Garfield | |
| 5,568,815 A | 10/1996 | Raynes et al. | |
| 5,581,369 A | 12/1996 | Righter et al. | |
| 5,606,978 A | 3/1997 | Armstrong et al. | |
| 5,623,939 A | 4/1997 | Garfield | |
| 5,776,073 A | 7/1998 | Garfield et al. | |
| 5,785,664 A | 7/1998 | Rosenberg | |
| 5,791,342 A | 8/1998 | Woodard | |
| 5,964,789 A | 10/1999 | Karsdon | |
| 5,991,649 A | 11/1999 | Garfield et al. | |
| 6,002,957 A | 12/1999 | Finneran | |
| 6,134,466 A | 10/2000 | Rosenberg | |
| 6,290,657 B1 | 9/2001 | Adams | |
| 6,421,558 B1 | 7/2002 | Huey et al. | |
| 6,434,420 B1 | 8/2002 | Taheri | |
| 6,529,569 B1 | 3/2003 | Corp et al. | |
| 6,748,263 B2 | 6/2004 | Griffiths et al. | |
| 6,816,744 B2 | 11/2004 | Garfield et al. | |
| 6,823,211 B2 | 11/2004 | Simpson et al. | |
| 6,879,858 B1 | 4/2005 | Adams | |
| 6,887,239 B2 | 5/2005 | Elstrom et al. | |
| 7,333,850 B2 | 2/2008 | Marossero et al. | |
| 7,447,542 B2 | 11/2008 | Calderon et al. | |
| 7,468,032 B2 | 12/2008 | Stahmann et al. | |
| 7,532,923 B1 | 5/2009 | Hayes-Gill et al. | |
| 7,616,980 B2 | 11/2009 | Meyer | |
| 7,689,275 B2 | 3/2010 | Hindenburg | |
| 7,758,522 B2 | 7/2010 | Pandit | |
| 7,828,753 B2 | 11/2010 | Euiano et al. | |
| 7,925,323 B2 | 4/2011 | Meyer | |
| 2002/0193670 A1 | 12/2002 | Garfield et al. | |
| 2005/0010127 A1 | 1/2005 | Calderon et al. | |
| 2005/0168343 A1* | 8/2005 | Longsdorf et al. | 340/664 |
| 2006/0015033 A1 | 1/2006 | Blakley et al. | |
| 2006/0189882 A1* | 8/2006 | Thomas | 600/546 |
| 2007/0213627 A1 | 9/2007 | James et al. | |
| 2008/0123771 A1* | 5/2008 | Cranford et al. | 375/285 |
| 2008/0139967 A1 | 6/2008 | Euliano et al. | |
| 2008/0183092 A1 | 7/2008 | Smith et al. | |
| 2008/0275316 A1 | 11/2008 | Fink et al. | |
| 2009/0036787 A1 | 2/2009 | James et al. | |
| 2009/0192396 A1 | 7/2009 | Hayes-Gill et al. | |
| 2010/0004548 A1 | 1/2010 | Rytky | |

OTHER PUBLICATIONS

Devedeux, Marque, Duchene, Germain, Mansour, "Uterine Electromyography: A Critical Review," Am. J. Obstet. Gynecol. 169:1636-1653, 1993.

Dill and Maiden, "The Electrical Potentials of the Human Uterus in Labor," Am. J. Obstet. Gynecol. 52:735-745, 1946.

Steer, "The Electrical activity of the Human Uterus in Normal and Abnormal Labor," Am. J. Obstet. Gynecol. 68:867-890, 1954.

Halliday and Heyns, "Uterine Activity and Electrical Response," J. Obstet. Gynaec. Brit. Emp. 62:155-161, 1955.

Hon and Davis, "Cutaneous and Uterine Electrical Potentials in Labor—an Experiment," Obstet. Gynec. 12:47-53, 1958.

Margue et al., "Uterine EHG Processing for Obstetrical Monitoring," IEEE Transactions on Biomedical Engineering, BME-33(12):1182-1186, Dec. 1986.

Larks SD, Dasgupta K.; "Wave Forms of the Electrohysterogram in Pregnancy and Labor," Am J Obstet Gynecol, May 1958; 75(5):1069-78.

Lucovnik M, Maner WL, Chambliss LR, Blumrick R, Balducci J, Novak-Antolic Z, Garfield RE. "Noninvasive uterine electromyography for prediction of preterm delivery," Am J Obstet Gynecol. Mar. 2011; 204(3):228.e1-10; Epub Dec 8, 2010.

Garfield RE, Maner WL, Mackay LB, Schlembach D, Saade GR.; "Comparing uterine electromyography activity of antepartum patients versus term labor patients," Am J Obstet Gynecol. Jul. 2005;193(1):23-9.

* cited by examiner

SKIN IMPEDANCE MATCHING SYSTEM AND METHOD FOR SKIN/ELECTRODE INTERFACE

CROSS REFERENCE TO RELATED APPLICATIONS

This application claims the benefit of U.S. Provisional Application No. 60/916,202, filed May 4, 2007 and is incorporated herein by reference.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

1. Field of the Invention

The present invention relates generally to medical devices and systems, and more particularly to medical devices for measuring skin characteristics that can vary on a patient-by-patient basis.

2. Description of the Related Art

The selectivity of the input impedance of an electronic system used in a medical environment is an important, though somewhat under emphasized feature of the overall monitoring device. As the sensitivity of electronic monitoring systems increase, it becomes increasingly important to consider the inaccuracy of measurements created by offset and gain errors caused by unknown or changing skin/electrode impedances. The effect is often significant enough to create an inability to monitor important electrical events during medical procedures. In several medical monitoring applications, an independent measurement of the patient skin/electrode impedance is made before initiation of electrical monitoring, to attempt to correct for the anticipated error caused by the impedance uncertainty. Even in the event of a pre-monitoring impedance measurement, no hardware or software solution exists to correct for the induced error. Furthermore, it has been established that the skin/electrode impedance can, and often does, change during an extended monitoring process. The present invention discloses a hardware/embedded software solution to continuously monitor the skin/electrode impedance and alter the input impedance of the monitoring circuitry to adapt to the changing mismatch between the patient and the electronics. The present invention can be implemented in a continuous monitoring mode or time defined monitoring mode to allow either real-time implementation of the impedance matching or predefined matching based upon the accuracy required by the medical procedure. Furthermore, the hardware matching circuitry can be implemented to provide a user defined impedance matching resolution through the addition of more resistors in the resistor ladder network.

Therefore, there remains a need for an improved system and method to match skin impedance under varying conditions.

BRIEF SUMMARY OF THE INVENTION

The present invention relates to a system for measuring the input impedance of a skin/electrode interface and selectively modifying the input impedance of the monitoring circuit to match the measured input impedance. The invention can provide a simplified method to an operator for correcting for input impedance mismatch between electronic monitoring circuitry and the skin/electrode interface than heretofore is believed to have been available. In accordance with one embodiment of the invention, an input impedance measuring circuit will interface with a microprocessor and a reconfigurable switch network to select the input impedance of the electronic monitoring circuitry, thus reducing the effect of impedance sensitivity of electrical instruments, such as EMG or EKG instruments.

BRIEF DESCRIPTION OF THE SEVERAL VIEWS OF THE DRAWINGS

A more particular description, briefly summarized above, may be had by reference to the embodiments illustrated in the appended drawings, forming part of the present specification and described herein. It is to be noted, however, that the appended drawings illustrate only some embodiments described herein and are therefore not to be considered limiting of the disclosure's scope, in that there can be other equally effective embodiments.

DETAILED DESCRIPTION

The present invention provides an impedance matching system and method that can provide relatively stable, impedance independent output voltages to electrical circuitry. The circuit can measure the skin impedance of a medical patient when each patient may have a different resistance than another patient. The invention can also provide a selectable accuracy based upon the number and value of resistors in the resistor ladder network. A microprocessor based control mechanism can activate the ladder network. In general, the system includes a first matching module or mode and a second sensing module or mode. The matching depends on the particular skin impedance detected and the switching of various resistors to match the skin impedance. The sensing mode, using the matched value of resistors generally for each electrode for a given circuit for the skin, is used to sense the relevant voltages through the skin and provide the voltage to a medical device for monitoring, analysis, or other medical procedure.

Figure 1:
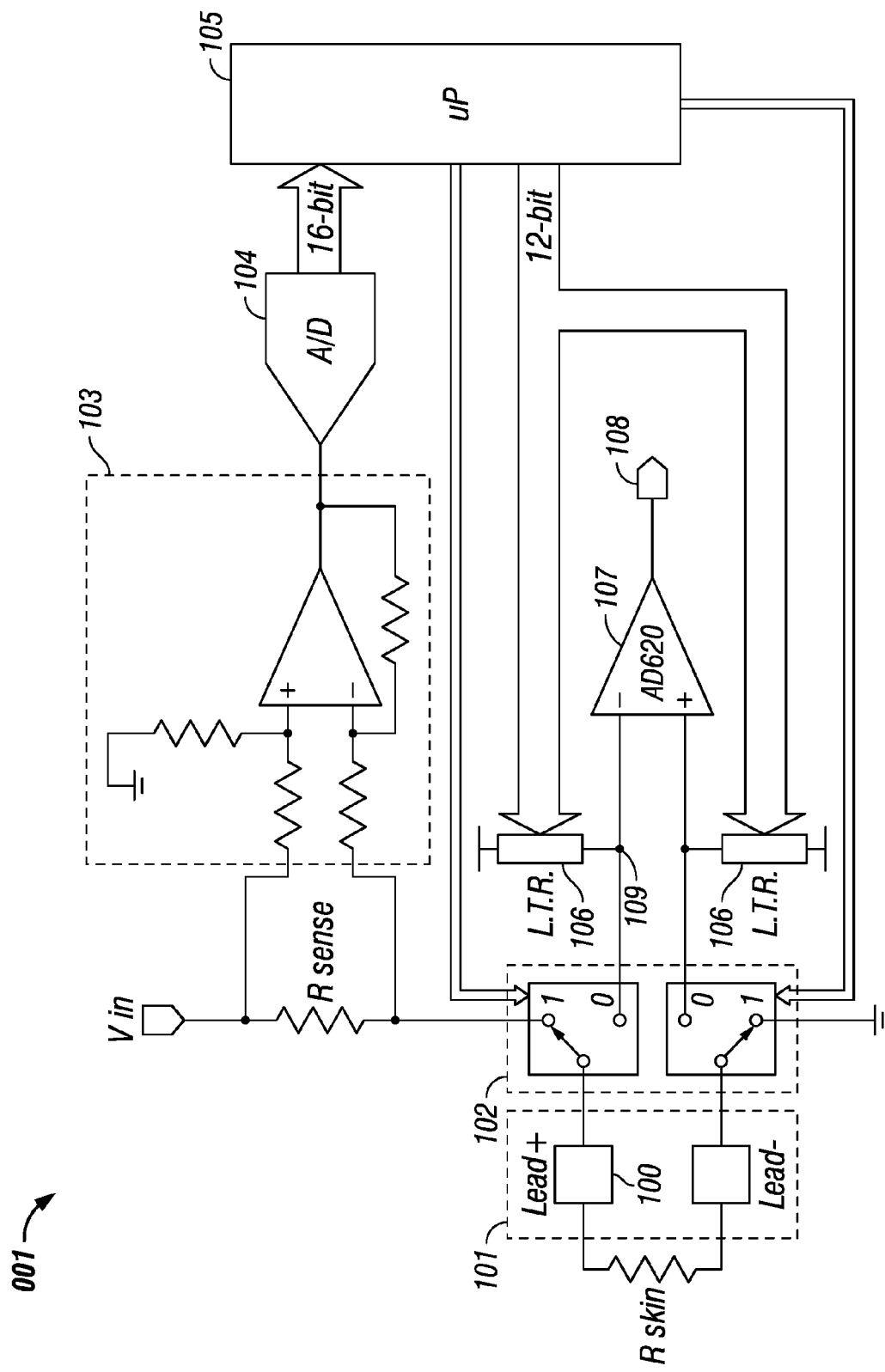
FIG. 1 is an exemplary schematic electrical circuit for a skin impedance matching system. In accordance with the present invention, a system 001 is described to measure the skin/electrode impedance and adaptively alter the input impedance of electrical monitoring circuitry to match the measured skin/electrode impedance. The measurement circuit in detail is comprised of skin/electrode interface 101, or sensing resistor, that can include electrodes or leads 100, a pair of switches 102, a current sensing differential amplifier 103, an analog to digital converter 104 and a microprocessor 105. The measurement circuit will sense the input impedance of the electrode/skin interface, amplify, digitize and provide information to the microprocessor. An embedded software routine will analyze the data in the microprocessor and generate a series of control signals to the resistor ladder network 106. For example, the control signals can be a 12-bit communications. A differential amplifier 107 can be utilized following the resistor ladder network to amplify the electrical signals generated by the medical patient. A medical device circuit 108, such as an EMG or EKG monitor, can be attached to the amplifier to obtain data from the electrodes. Multiple circuits can be progressively switched using the same electrodes if appropriate. In some embodiments, the amplifier will not be used and in other embodiments, an amplifier is integral with the medical device 108 and is not a separate element.

FIG. 1 is an exemplary schematic electrical circuit for a skin impedance matching system. In accordance with the present invention, a system 001 is described to measure the skin/electrode impedance and adaptively alter the input impedance of electrical monitoring circuitry to match the measured skin/electrode impedance. The measurement circuit in detail is comprised of skin/electrode interface 101 that can include electrodes or leads 100, a pair of switches 102, a current sensing differential amplifier 103, an analog to digital converter 104 and a microprocessor 105. The measurement circuit will sense the input impedance of the electrode/skin interface, amplify, digitize and provide information to the microprocessor. An embedded software routine will analyze the data in the microprocessor and generate a series of control signals to the resistor ladder network 106. For example, the control signals can be a 12-bit communications. A differential amplifier 107 can be utilized following the resistor ladder network to amplify the electrical signals generated by the medical patient. A medical device circuit 108, such as an EMG or EKG monitor, can be attached to the amplifier to obtain data from the electrodes. Multiple circuits can be progressively switched using the same electrodes if appropriate. In some embodiments, the amplifier will not be used and in other embodiments, an amplifier is integral with the medical device 108 and is not a separate element.

Figure 2:
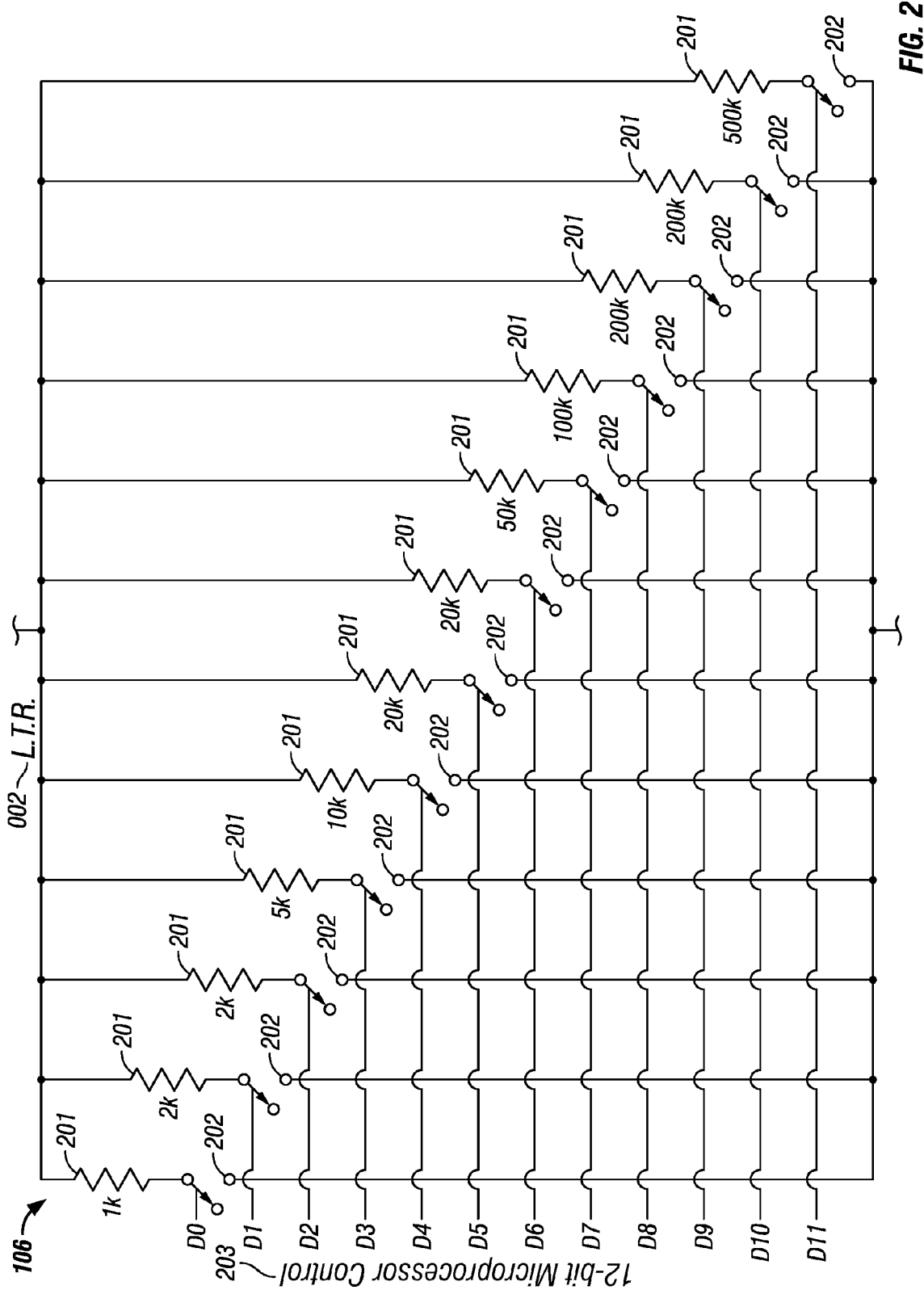
FIG. 2 is an exemplary electrical schematic of a resistor ladder network.

FIG. 2 is an exemplary electrical schematic of a resistor ladder network. In accordance with the present invention, a resistor ladder network 106, also shown in FIG. 1, is described which includes resistors 201 and microcontroller activated switches 202 to implement any combination of resistors in parallel, thus allowing extreme accuracy in the total impedance generated by the combined resistor ladder.

In the present invention, an advantageous mode of operation is described briefly referencing the elements in FIGS. 1 and 2. Upon the application of the electrodes to the patient skin surface, and the attachment of the electrode cable to the electronic monitoring system 001, the microprocessor 105 can set both of microcontroller activated switches 102 to the ON or 1 position, creating a current flow path from Vin, through $R_{sense}$, $R_{lead+}$, $R_{skin}$, $R_{lead-}$ to ground. The microprocessor can communicate to the switches with for example 2-bit or even 1-bit signals. The voltage drop, and thus the current through the $R_{sense}$ resistor is measured and amplified by the current sensing differential amplifier 103. The analog signal is then digitized by the A/D converter 104 and passed in a multi-bit format to the microprocessor 105. An embedded software routine in the microprocessor analyzes the digitized information and calculates the resistive load applied by the skin electrode interface described by 101.

The microprocessor creates a set of control signals 203 in FIG. 2 and sends them to the resistor ladder network 106 to activate switches 202 as needed to create a set of parallel resistors that will create an overall resistive load corresponding to the resistive load created by the skin/electrode interface 101 in FIG. 1. Upon completion of the resistive matching operation, the microprocessor sets the input switches 102 back to the 0 or OFF position to return the electronic system to regular operation as a medical monitoring device, while leaving the resistor ladder network programmed to continuously match the electrode/skin impedance, thereby continuously calibrating the incoming electrical signals using the resistor ladder network 106. For example, and without limitation, the exemplary values of resistors disclosed in FIG. 2 can create a variety of resistance values by various combinations of switches that are no more than a 5% variance with any skin impedance generally between 10K ohms to 100K ohms. Due to the matching, the voltage from monitoring the skin through the electrodes is split at the junctions 109 where a portion of the voltage flows through the network 106 and the other portion flows through the amplifier 107. If additional voltage is needed for the device 108, the voltage can be amplified accordingly.

The figures described above and the written description of specific structures and processes below are not presented to limit the scope of what Applicants have invented or the scope of the appended claims. Rather, the Figures and written description are provided to teach any person skilled in the art to make and use the inventions for which patent protection is sought. Those skilled in the art will appreciate that not all features of a commercial implementation of the inventions are described or shown for the sake of clarity and understanding. Persons of skill in this art also appreciate that the development of an actual commercial embodiment incorporating aspects of the present inventions will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation, location and from time to time. While a developer's efforts might be complex and time-consuming in an absolute sense, such efforts would be, nevertheless, a routine undertaking for those of skill this art having benefit of this disclosure. The inventions disclosed and taught herein are susceptible to numerous and various modifications and alternative forms. Further, the use of a singular term, such as, but not limited to, "a," is not intended as limiting of the number of items. The use of relational terms, such as, but not limited to, "top," "bottom," "left," "right," "upper," "lower," "down," "up," "side," and the like are used in the written description for clarity in specific reference to the Figures and are not intended to limit the scope of the invention or the appended claims. The term "coupled," "coupling," "coupler," and like terms are used broadly herein and can include any method or device for securing, binding, bonding, fastening, attaching, joining, inserting therein, forming thereon or therein, communicating, or otherwise associating, for example, mechanically, magnetically, electrically, chemically, directly or indirectly with intermediate elements or by wireless transmission, one or more pieces of members together and can further include without limitation integrally forming one functional member with another in a unity fashion. The coupling can occur in any direction, including rotationally.

Other and further embodiments utilizing one or more aspects of the inventions described above can be devised without departing from the spirit of Applicant's invention. For example and without limitation, other embodiments of the system and method can include manual selection of the resistance values, and other embodiments can include a variable resistor that can be adjusted to match the skin impedance. Further, the embodiments can be combined to produce other variations. Discussion of singular elements can include plural elements and vice-versa.

The order of steps can occur in a variety of sequences unless otherwise specifically limited. The various steps described herein can be combined with other steps, interlineated with the stated steps, and/or split into multiple steps.

Similarly, elements have been described functionally and can be embodied as separate components or can be combined into components having multiple functions.

The inventions have been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicants, but rather, in conformity with the patent laws, Applicants intend to protect fully all such modifications and improvements that come within the scope or range of equivalent of the following claims. Further, unless the context requires otherwise, the word "comprise" or variations such as "comprises" or "comprising", should be understood to imply the inclusion of at least the stated element or step or group of elements or steps or equivalents thereof, and not the exclusion of a greater numerical quantity or any other element or step or group of elements or steps or equivalents thereof.

What is claimed is:

1. A system for matching skin impedance of a patient, comprising:
    a first module adapted to determine the skin impedance of the patient by sensing an input impedance from the patient through electrodes, and amplifying and digitizing the input impedance;
    a resistor ladder network communicably coupled to the first module;
    a microprocessor configured to analyze the input impedance and generate a series of control signals to direct the resistor ladder network to match the skin impedance of the patient; and
    a second module adapted to sense electrical signals from the patient through electrodes coupled to the patient's skin, wherein the electrical signals are sensed with the resistor ladder network matching the skin impedance of the patient.

2. The system as set forth in claim 1, wherein the first and second modules use identical electrodes.

3. The system as set forth in claim 1, wherein the first module comprises a sensing resistor, an amplifier, and an analog to digital converter.

4. The system as set forth in claim 1, further comprising a pair of switches controlled by the microprocessor for switching between the first and second modules.

5. The system as set forth in claim 1, wherein the resistor ladder network is digitally configured by the microprocessor through the control signal.

6. The system as set forth in claim 1, wherein the second module provides the electrical signals to an external medical device.

7. The system as set forth in claim 6, wherein the electrical signals are calibrated by the second module using the resistor ladder network.

8. The system as set forth in claim 6, wherein the external medical device includes an electromyography (EMG) monitor.

9. A method for matching skin impedance of a patient, comprising:
    applying at least one pair of electrodes to a skin of the patient, and coupling the at least one pair of electrodes to an impedance measurement module;
    switching microcontroller activated switches in the impedance measurement module to a matching mode;
    determining the skin impedance of the patient by measuring a voltage drop between the at least one pair of electrodes;
    switching a resistor ladder network in the impedance measurement module to match the determined skin impedance of the patient;
    switching the microcontroller activated switches to a sensing mode;
    measuring voltage inputs from the skin of the patient; and
    calibrating the voltage inputs using the resistor ladder network to obtain calibrated inputs.

10. The method as set forth in claim 9, wherein the determining and measuring steps are performed using identical electrodes.

11. The method as set forth in claim 9, further comprising providing the calibrated inputs to an external medical device.

12. The method as set forth in claim 11, wherein the external medical device includes an electromyography (EMG) monitor.

13. The method as set forth in claim 11, wherein the steps of switching microcontroller activated switches to a matching mode and determining the skin impedance by measuring the voltage drop between the at least one pair of electrodes is performed by a microprocessor interposed between the patient and the external medical device.

14. The method as set forth in claim 13, wherein the resistor ladder network is digitally configured by the microprocessor through a plurality of control signals.

* * * * *